(12) United States Patent
Kanehara et al.

(10) Patent No.: US 8,030,020 B2
(45) Date of Patent: Oct. 4, 2011

(54) PROCESS FOR PREPARING LIVE SMALLPOX VACCINE

(75) Inventors: Tomomi Kanehara, Kumamoto (JP); Hiroyuki Yokote, Kumamoto (JP); Kunio Ohkuma, Kumamoto (JP); Masahiko Kuranaga, Kumamoto (JP); Shigeru Morikawa, Musashimurayama (JP)

(73) Assignees: Juridicial Foundation The Chemo-Sero-Therapeutic Research Institute, Kumamoto-Shi (JP); Japan as represented by Director General of National Institute of Infectious Diseases, Tokyo-To (JP)

( * ) Notice: Subject to any disclaimer, the term of this patent is extended or adjusted under 35 U.S.C. 154(b) by 244 days.

(21) Appl. No.: 12/376,625

(22) PCT Filed: Aug. 6, 2007

(86) PCT No.: PCT/JP2007/065370

§ 371 (c)(1), (2), (4) Date: Mar. 4, 2009

(87) PCT Pub. No.: WO2008/018411

PCT Pub. Date: Feb. 14, 2008

(65) Prior Publication Data

US 2010/0183672 A1 Jul. 22, 2010

(30) Foreign Application Priority Data

Aug. 7, 2006 (JP) ................................ 2006-214017

(51) Int. Cl.
*C12P 1/00* (2006.01)
*C12N 5/00* (2006.01)

(52) U.S. Cl. ......................................... 435/41; 435/325

(58) Field of Classification Search ........................ None
See application file for complete search history.

(56) References Cited

U.S. PATENT DOCUMENTS 4,992,374 A 2/1991 Sugimoto et al.
2007/0298054 A1 12/2007 Shida et al.

FOREIGN PATENT DOCUMENTS

JP 63036777 A 2/1988
WO 2005054451 A1 6/2005

OTHER PUBLICATIONS

Supplementary European Search Report in EP 07 792 040.3 dated Jul. 29, 2010.

Sugimoto and Yamanouchi, "Characteristics of an attenuated vaccinia virus strain, LC16m0, and its recombinant virus vaccines," Vaccine 12(8):675-681 (Jan. 1, 1994).

Watanabe et al, "Stability of recombinant vaccinia virus LC16m0 or LC16m8: Preserved laboratory attenuation markers and conserved expression of inserted HBsAg gene," Vaccine 7(6): 499-502 (Dec. 1, 1989).

Takahashi-Nishimaki et al.,"Genetic analysis of vaccinia virus lister strain and its attenuated mutant LC16m8: production of intermediate variants by homologous recombination," J Gen Virol, 1987, pp. 2705-2710, vol. 68, No. 10.

Moss,"Poxviridae: the viruses and their replication," Virology, 2001, pp. 2849-2883, Lippincott Williams & Wilkins, Philadelphia, PA.

Fukuda et al.,"Pathology of postvaccinal encephalitis," clinics and virus, 1974, pp. 53-58, vol. 2.

Hashizume,"Basis of new attenuated vaccine lymph LC16m8 strain," clinics and virus, 1975, pp. 13-19, vol. 3.

Hashizume et al.,"Properties of attenuated mutant of vaccinia virus, LC16m8, derived from lister strain," Vaccinia virus as vectors for vaccine antigens, 1985, pp. 87-99, Ed. Elsevier Science Publishing Co., Inc., New York, NY.

Kuboya,"Evaluation for adult inoculation of dried cell culture vaccinia vaccine 'LC16 Chiba'," Chiba prefectural institute of public health report, 2004, pp. 11-14, No. 28.

Takahashi-Nishimaki et al.,"Regulation of plaque size and host range by a vaccinia virus gene related to complement system proteins," Virology, 1991, pp. 158-164, vol. 181.

Engelstad et al.,"The vaccinia virus 42-kDa envelope protein is required for the envelopment and egress of extracellular virus and for virus violence," Virology, 1993, pp. 627-637, vol. 194.

Kidokoro et al.,"Genetically stable and fully effective smallpox vaccine strain constructed from highly attenuated vaccinia LC16m8," Proc. Natl. Acad. Sci., 2005, pp. 4152-4157, vol. 102, No. 11.

Saijo et al.,"Growth test of LC16m8 strain including LC16m0-type revertant virus in rat skin test, Study subsidy in welfare and labor science, special research project of welfare and labor science, study on quality management of cell culture vaccinia vaccine (H15-Tokubetsu-43)," 2003, pp. 33-39.

*Primary Examiner* — Albert Navarro
(74) *Attorney, Agent, or Firm* — Browdy and Neimark, PLLC

(57) ABSTRACT

A safer live smallpox vaccine, which contains a lowered content of revertants, is provided. A process for manufacturing a live smallpox vaccine which comprises steps of: inoculating a master seed solution of an attenuated vaccinia virus to an appropriate number of containers (1 to n wherein n is an integer) of rabbit kidney cells and incubating them; inoculating a portion of the cultured solution obtained from each container to RK-13 cells and to Vero E6 cells and incubating them to thereby select containers which contain a cultured solution that forms plaques in RK-13 cells but not in Vero E6 cells; and preparing a drug substance of vaccine using the aforementioned cultured solution (working seed solution), and a live smallpox vaccine prepared in the aforementioned process.

12 Claims, 3 Drawing Sheets

PROCESS FOR PREPARING LIVE SMALLPOX VACCINE

TECHNICAL FIELD

The present invention relates to a process for manufacturing a live smallpox vaccine containing an attenuated vaccinia virus as an active ingredient, which shortly produces revertants while proliferating. More specifically, the present invention relates to a process for manufacturing a live smallpox vaccine, which comprises steps of: inoculating a master seed solution containing an attenuated vaccinia virus to an appropriate number of containers (1 to n wherein n is an integer) of rabbit kidney cells and culturing them; inoculating a portion of the cultured solution from each container to RK-13 cells and to Vero E6 cells and culturing them to thereby select containers which contain cultured solution that forms plaques in RK-13 cells but not in Vero E6 cells and pooling each cultured solution obtained from the selected containers; and preparing a drug substance of vaccine using the aforementioned pooled cultured solution (working seed solution), as well as a live smallpox vaccine manufactured in the aforementioned process.

BACKGROUND ART

Smallpox, also called variola, is one of infectious viral diseases which were once most feared. Viruses classified into *Orthopoxvirus* genus including variola virus have a genome of about 180 to 200 kbp in length, which has a region of about 100 kbp in its central part and well preserved among viruses classified into *Orthopoxvirus* genus. Since protective antigens are coded in this region, viruses classified into *Orthopoxvirus* genus exhibit almost complete cross immunity (see e.g. Non-patent reference 1) among them. Generally, an attenuated strain derived from a pathogenic virus is used for the manufacturing of a live vaccine. In case of smallpox vaccines (variola vaccines), however, vaccinia viruses, not the viruses derived from smallpox viruses, typically, Lister strain, New York City Board of Health strain (hereinafter also referred to as "NYCBH strain"), Dairen strain, Ikeda strain, etc. have been used.

In Japan, smallpox vaccines, which were manufactured from bovine skin tissues with vesicles generated by inoculating the Lister strain or the Dairen/Ikeda strain to cattle, had been used. These vaccines had caused serious side effects such as postvaccinal encephalitis in infants receiving the first dose at a ratio of several to a million (see e.g. Non-patent reference 2). They were not sterile, as cattle were used for the propagation and passage, and contained non-purified viruses. Thus, Hashizume et al. prepared temperature-sensitive attenuated virus strains originated from the Lister strain adapting the virus to primary cells of rabbit kidney and to a lower temperature. In the end, the LC16m8 strain, which formed small pocks in the chorioallantoic membrane of chicken egg, was selected from clones and purified. The LC16m8 strain was approved in Japan in 1975 after clinical trials (see e.g. Non-patent reference 3). Although the attenuated vaccinia virus LC16m8 strain has a extremely lower neurovirulence than that of its parent strain, the Lister strain, or the NYCBH strain which is a parent strain of a smallpox vaccine Dryvax approved in the U.S. (see e.g. Non-patent references 3 and 4), the level of neutralizing antibodies induced by the LC16m8 strain was almost comparable to the level of those induced by the Lister strain (see e.g. Non-patent reference 5). Also, it is only the LC16m8 strain that is approved as an attenuated smallpox vaccine manufactured in cell culture.

The LC16m8 strain was selected as a virus which formed small pocks after being passaged for three times at a lower temperature originated from its parent strain, the LC16mO strain, and was cloned. It has been revealed that the cause of forming such small pocks is the deficiency of B5R protein due to a frame-shift mutation occurred in the B5R gene (see e.g. Non-patent reference 6). It is reported that, since the B5R protein is a major constituent protein of the extracellular membrane of the viruses classified into *Orthopoxvirus* genus, the deficiency of this protein may results in the reduced efficiency of viral infection to neighboring cells and thereby in the small pocks (see e.g. Non-patent reference 7).

On the other hand, since the deficiency of B5R protein is due to the deletion of a single nucleotide in the B5R gene, LC16mO-typed reversionary strains (revertants) appear comparatively shortly (see e.g. Non-patent reference 8). A nucleotide sequence analysis of the B5R gene of these revertant strains revealed that the reading frame of ORF of B5R was reverted due to a duplication of a single nucleotide, a duplication of four nucleotides or a deletion of two nucleotides in the adjacent of the nucleotide 274G. When compared on biological properties, the revertant strains formed plaques that were smaller in size than those of the LC16mO strain but larger than those of the LC16m8 strain in RK-13 cells and Vero E6 cells. They also formed pocks on the chorioallantoic membrane of embryonated chicken egg equivalent in size to those of LC16mO. There was no significant difference in the proliferative ability of the virus in rabbit skin, which is thought to be correlated to the proliferative ability in human skin, when the revertant content was up to around 4%. Meanwhile, it was presumed that there was a significant difference in the proliferative ability when the revertant content became much higher (see e.g. Non-patent reference 9).

Non-patent reference 1: Moss, B. 2001. Poxyiridae: the viruses and their replication, p. 2849-2883. In D. M. Knipe and P. M. Howley (ed.), Fields virology, 4th ed., vol. 2. Lippincott/The Williams & Wilkins Co., Philadelphia, Pa.

Non-patent reference 2: Yoshiro Fukuda, Toshitaka Takagi: Pathology of postvaccinal encephalitis, Clinics and Virus 2:53-58, 1974

Non-patent reference 3: So Hashizume: Basis of new attenuated vaccine lymph LC16m8 strain, Clinics and Virus 3:13-19, 1975

Non-patent reference 4: Hashizume S., Yoshizawa H., Morita M., Suzuki K.: Properties of attenuated mutant of vaccinia virus, LC16m8, derived from Lister strain. Vaccinia Virus as Vectors for Vaccine Antigens, Quinnan, Ed. Elsvier Scienced Publishing Col, Inc 87-99, 1985

Non-patent reference 5: Hiroko Kuboya: Evaluation for adult inoculation of dried cell culture vaccinia vaccine "LC16•Chiba", Chiba Prefectural Institute of Public Health Report No. 28, 11-14, 2004

Non-patent reference 6: Takahashi-Nishimaki, Funahashi F., Miki S. et al.: Regulation of plaque size and host range by a vaccinia virus gene related to complement system proteins. Virology 181: 158-164, 1991

Non-patent reference 7: Engelstad M. and Smith G.: The vaccinia virus 42-kDa envelope protein is required for the envelopment and egress of extracellular virus and for virus virulence. Virology 194, 627-637, 1993

Non-patent reference 8: Kidokoro, M., M. Tashiro, and H. Shida. 2005. Genetically stable and fully effective smallpox vaccine strain constructed from highly attenuated vaccinia LC16m8. Proc. Natl. Acad. Sci. USA 102:4152-4157, 2005

Non-patent reference 9: Masayuki Saijo et al., Growth test of LC16m8 strain including LC16mO-type revertant virus in rat skin test, Study subsidy in welfare and labor science, Special Research Project of Welfare and Labor Science, Study on quality management of cell culture vaccinia vaccine (H15-Tokubetsu-43), 2003

DISCLOSURE OF THE INVENTION

Technical Problem to be Solved by the Invention

Figure 1:
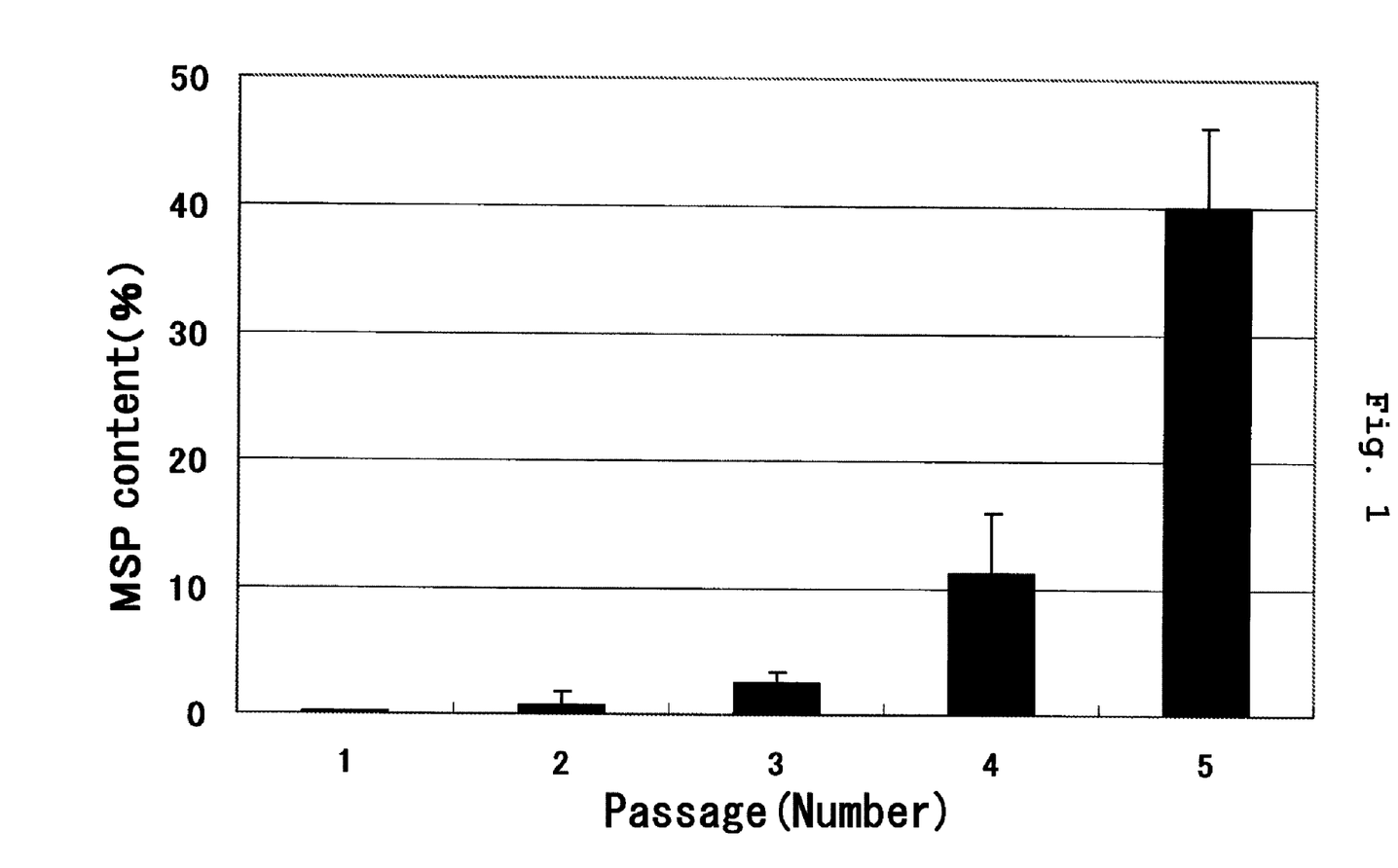
FIG. 1 is a graph showing the changes in MSP content in the cultured solution of the LC16m8 strain virus at each number of passage.

As described above, in multiple passaged culture of the vaccinia virus LC16m8 strain in primary cells of rabbit kidney, revertants (hereinafter also referred to as "MSP strain") which form plaques slightly larger than small plaques characterized as the LC16m8 strain (medium size plaques; hereinafter also referred to as "MSP") come to appear. Since the content ratio of MSP strain increases with the number of passage (cf. FIG. 1), it is difficult to remove MSP strain by conducting limiting dilution or plaque isolation as commonly used in viral cloning. Accordingly, the object of the present invention is to manufacture a live smallpox vaccine which is safe as it contains a reduced content of MSP, and to provide a process for manufacturing the vaccine as well.

Means for Solving the Problems

Under the circumstances, the present inventors have earnestly continued research activities in order to solve the problems described above and as a result have found that MSP strain may be selected and excluded by using RK-13 cells and Vero E6 cells since the proliferative ability of LC16m8 strain in RK-13 cells and Vero E6 cells is different from that of MSP strain. Specifically, the LC16m8 strain forms small size plaques in RK-13 cells easily recognized by visual observation whereas it forms only needle-sized plaques in Vero E6 cells that are hardly recognized by visual observation. On the other hand, the MSP strain forms medium sized plaques in both RK-13 cells and Vero E6 cells. Besides, the present inventors have succeeded in reducing the MSP content in the drug substance of vaccine by using a viral solution as a working seed, which formed plenty of plaques in RK-13 cells but did not form plaques of MSP strain in Vero E6 cells when the virus was made infect RK-13 cells and Vero E6 cells at a certain range of MOI, and thus completed the present invention. Accordingly, the present invention provides a cell-cultured live smallpox vaccine as well as a process for manufacturing the vaccine as shown below:

1. A process for preparing a working seed solution of a vaccine containing as an active ingredient a mutant virus that is likely to generate revertants, which comprises the following steps (1) to (3):

(1) Inoculating a solution of a mutant virus to 1 to n containers, wherein n is an integer, of animal cells and incubating them;

(2) Diluting a portion of the cultured solution from each container and inoculating the diluted solution to RK-13 cells and to Vero cells and incubating them;

(3) Selecting containers which contain a cultured solution that forms plaques in RK-13 cells but does not form plaques in Vero cells and pooling each cultured solution obtained from selected containers.

2. The process of 1 above wherein a viral content of the diluted solution in (2) above is $1 \times 10^4$ PFU or more.
3. The process of either 1 or 2 above wherein the animal cells are primary cells.
4. The process of 3 above wherein the primary cells are derived from rabbit kidney.
5. The process of any one of 1 to 4 above wherein the mutant virus is an attenuated vaccinia virus.
6. The process of 5 above wherein the attenuated vaccinia virus is the LC16m8 strain.
7. A process for manufacturing a smallpox vaccine which comprises inoculating the working seed solution obtained through the process of either 5 or 6 above to animal cells and incubating them and then collecting a viral solution from the culture.
8. The process of 7 above wherein the concentration is a MOI of 0.001 to 5, preferably 0.1 to 1, at which the working viral solution is inoculated and wherein the number of the animal cells is $1 \times 10^5$ to $1 \times 10^{12}$, preferably $0.5 \times 10^8$ to $3 \times 10^8$.
9. The process of either 7 or 8 above wherein the animal cells are primary cells.
10. The process of 9 above wherein the primary cells are derived from rabbit kidney.
11. A live smallpox vaccine manufactured though the process of any one of 7 to 10 above.
12. The live smallpox vaccine of 11 above wherein a content ratio of revertant is 3% or less.

More Efficacious Effects than Prior Art

According to the present invention, a live smallpox vaccine containing an attenuated vaccinia virus as an active ingredient and a reduced content of MSP strain is provided. As for the live smallpox vaccine manufactured according to the present invention, the adverse side effects caused by MSP strain are eliminated since the content of MSP strain is reduced. Thus, when administered to human, severe dermal reactions may be prevented. Also, according to the process of the present invention, a process for manufacturing a drug substance of vaccine with a reduced content of MSP strain is provided. The process may be used not only for a drug substance of vaccine containing an attenuated vaccinia virus but also for preparing a drug substance of vaccine containing other viruses likely to generate revertants while being cultured.

BEST MODE FOR CARRYING OUT THE INVENTION

The process described in the present invention is characterized by preparing a working seed solution containing a reduced content of revertants, from a master seed solution of an attenuated vaccinia virus with the use of animal cells and by preparing a drug substance of vaccine from the aforementioned working seed solution.

The present invention is explained herein chiefly for attenuated vaccinia virus. However, not limited to vaccinia virus, the present invention may be applicable to any virus that is artificially mutated by a certain method, e.g. genetic engineering, adaptation to a lower temperature, serial passage in heterologous cells, UV radiation or irradiation, or is naturally mutated (hereinafter also referred to as "mutant virus") and that shortly generates revertants while being cultured. As defined herein, a revertant is a virus, which lost a part or all of properties acquired when a mutation occurred in the virus, and regained a part or all of properties which the virus had once possessed before the mutation. Such properties include, for instance, ability to form plaques, plaque size, pock size, pathogenicity, proliferative ability, temperature sensitivity, host sensitivity, tissue-tropism, proliferative ability in the skin, neurovirulence, and the like.

As for animal cells to be used in the present invention, any animal cells may be used insofar as a mutant virus of interest may proliferate therein. Preferably, animal cells to be used may be those derived from human lung, human amnion, monkey kidney, rabbit kidney, canine kidney, or chicken embryo, which have been used in manufacturing vaccines. In case that an attenuated vaccinia virus is propagated, primary rabbit kidney cells prepared from rabbit kidney may preferably be used. Animal cells may be prepared as routinely been done in the art. For instance, a suspension of primary rabbit kidney cells may be prepared as described below. The kidneys are removed from 7-day old SPF suckling rabbits, washed with a phosphate buffer containing 400 mg titer/L of streptomycin sulfate and 50 mg titer/L of erythromycin (hereinafter also referred to as "PBS(−)/2ES"), and cut into pieces of about 1 to 2 mm with scissors. The pieces are again washed with PBS (−)/2ES, put in Hanks' balanced salt solution containing 0.3% of disperse, 0.5% of lactalbumin and 4.5% of fetal bovine serum (hereinafter also referred to as "disperse solution") and incubated at 4° C. overnight while being stirred for digestion. After digestion, the disperse solution is removed by centrifugation and cell precipitates are suspended in an appropriate medium resulting in a suspension of primary rabbit kidney cells. If filtration is further performed with a mesh, a uniform suspension of cells may be obtained.

As for culture media used for cell cultivation includes agar media and liquid media, in view of their form, and M-199, MEM, YMM-01, DMEM, RPMI, cMEM, balanced salt solution and the like, in view of their type, and may appropriately be selected depending on cells, the purpose of cultivation or the stage of cultivation. Preferably, Hanks' balanced salt solution containing 0.5% of lactalbumin, 5% of fetal bovine serum and 5% of bovine calf serum may be used. Culture media used for cell expansion (hereinafter also referred to as "growth medium") may contain sera, amino acids, vitamins, sugars, antibiotics, pH adjusting buffers, and the like.

After being confirmed a full growth of cells, cells are inoculated with viruses. The growth medium is removed by aspiration. Cells are washed with a phosphate buffer containing 0.01% of magnesium dichloride, 0.014% of calcium dichloride, 200 mg titer/L of streptomycin sulfate and 25 mg titer/L of erythromycin (hereinafter also referred to as "PBS (−)/ES") and then added with a viral solution diluted to a suitable concentration. Cells are put at 30° C. for 1 to 2 hours until viruses are sufficiently adsorbed to the cells. Subsequently, a culture medium used for viral proliferation (hereinafter also referred to as "maintenance medium") is added and incubation of the cells is performed. A maintenance medium may be a serum free medium or a medium with a low protein content. Preferably, 199 medium containing 200 mg titer/L of streptomycin sulfate, 25 mg titer/L of erythromycin and 0.2% of gelatin, is used. A pH range of 6 to 8 and a temperature in a range of 30° C. to 39° C. may be set. The amount of a culture medium, additives and duration of incubation may appropriately be determined depending on the culture scale.

In the working examples of the present invention, the LC16m8 strain established by Hashizume et al. (Clinics and Virus Vol. 3, No. 3, p. 229-235, 1975) is used as a master seed solution of attenuated vaccinia virus. The LC16m8 strain is a temperature-sensitive mutant obtained from the clinically isolated Lister strain. It cannot proliferate at more than 40.8° C. and has a property to form small pocks on the chorioallantoic membrane of embryonated chicken egg. When the LC16m8 strain is serially subjected to passage in animal cells, revertants (MSP strain) which form medium size plaques appear. The master seed solution of LC16m8 strain was provided from The Chiba Prefectural Serum laboratory.

A working seed solution may be prepared through the steps: inoculating a master seed solution of LC16m8 strain to an appropriate number (1 to n; n is an integer) of containers containing primary cells of rabbit kidney and incubating them; inoculating a portion of the cultured solution from each container to RK-13 cells and to Vero E6 cells and incubating them; selecting containers which contain a cultured solution that forms plaques in RK-13 cells but does not form plaques of MSP in Vero E6 cells when 10,000 PFU or more of viruses are inoculated, and pooling each cultured solution obtained from the selected containers. When a master seed solution is inoculated to primary cells of rabbit kidney, a viral infectivity titer of MOI=0.001 to 0.3 may be used as commonly used for propagating viruses. Preferably, it is in a range of MOI=0.003 to 0.01. In case that a master seed solution already contains a certain content of MSP strain, it is preferable to use such a range of MOI as to avoid contamination of MSP strain. For instance, when MSP strain is present at a ratio of $10^{-5}$ in a master seed solution, the amount of LC16m8 strain to be inoculated to a container may be adjusted theoretically so as not to exceed $10^5$ PFU. Practically, the number of cells to be used for propagating the virus is increased or MOI for inoculation is lowered depending on the content of MSP strain.

When a suspension of primary cells of rabbit kidney is added to a container (a plate, a flask, a roller bottle, etc.), $1 \times 10^5$ to $1 \times 10^9$ cells, preferably about 3 to $6 \times 10^6$ cells, may be used. An appropriate number (1 to n) of containers may be determined depending on the manufacturing scale of a drug substance of vaccine.

More specifically, the following procedures will apply. A suspension of primary cells of rabbit kidney prepared in a growth medium is added to an appropriate number of containers and cultured until the cells form a monolayer sheet. A master viral seed solution diluted in a maintenance medium is added into containers which are incubated until plenty of cytopathic effects are observable and then freezing/thawing is performed for the containers. A small amount of a viral solution is taken from each of the containers and tested for the detection of MSP strain. The containers are stored frozen at −80° C. until results of the detection test are obtained.

For the detection of MSP strain, an established cell line derived from the kidney of African green monkey (Vero cells) and an established cell line derived from rabbit kidney (RK-13 cells) may be used. The LC16m8 strain forms small sized plaques in RK-13 cells but forms only needle-sized plaques in Vero E6 cells. On the other hand, MSP strain, i.e. revertants of the LC16m8 strain, forms medium size plaques (MSP) in both Vero and RK-13 cells. Utilizing this property, MSP strain may be detected. A cultured solution containing the virus from each of the containers is appropriately diluted in an MEM medium containing 1% of inactivated FBS and inoculated to a monolayer sheet of Vero cells and that of RK-13 cells and thereto is overlaid an MEM medium containing 5% of inactivated FBS and 0.6% of agarose and those cells are incubated. A cultured solution from each container is diluted 10 to 5,000 folds, preferably 100 to 2,000 folds, so that a suitable amount of the virus for plaque assay may be obtained. In case that the viral amount is checked with the use of RK-13 cells, a culture solution is diluted 1,000 to 100,000 folds. A cultured solution is collected from each of the containers, which forms plaques in RK-13 cells but not in Vero cells when 10,000 PFU or more of viruses of cultured solution is inoculated. A content ratio of MSP strain to a whole viral amount may be calculated from the numbers of plaques occurring in each of Vero and RK-13 cells for each cultured solution. Among those, cultured solutions, which possess a suitable titer and contain a decreased content of MSP strain, may be selected. A viral solution which contains MSP strain at a concentration of 0.015% or less to the whole viral amount, preferably of 0.01% or less, may be used as a working seed solution for preparing a drug substance of vaccine. Viral solutions obtained from the selected containers may optionally be pooled depending on the culture scale.

The thus obtained working seed solution is used for preparing a drug substance of vaccine. As the method of culturing cells, culturing stand still, culturing in roller bottles, culturing suspended cells and the like are known. For the culturing suspended cells, a microcarrier for adhering cells is sometimes used. For a microcarrier, a variety of microbeads with different size, shape, density, surface charge or surface coating material are commercially available and may be used as appropriate. It includes for instance microbeads such as e.g. Cytodex, Biocylon (Nalge Nunc International) and CEL-LYARD (PENTAX), which may appropriately be used depending on cell types or conditions to be used. In case of Cytodex (Cytodex I, Amersham Bioscience), it may be used at an amount of 1 to 10 g, preferably 3 to 5 g, per 1 L of culture.

The inoculation of a virus to cells may be carried out at a range of MOI=0.001 to 5, preferably MOI=0.1 to 1. The temperature and duration of incubation for cell cultivation and viral propagation may be adjusted depending on a combination of cell types, an amount of viruses to be inoculated, scale and means of cultivation and the like. By way of example, the cultivation in roller bottles using the above working seed solution in primary cells of rabbit kidney may be performed as described below.

A suspension of primary cells of rabbit kidney in a growth medium is added at 1 to $2 \times 10^8$ cells/roller bottle and cultured at 37° C. for 4 to 6 days. After being confirmed that cells formed a monolayer sheet, the medium is removed by aspiration and the cells are washed with PBS/ES. A viral solution diluted to an appropriate concentration with a maintenance medium (MOI=0.1 to 1) is added thereto and left at 30° C. for 1 to 2 hours on a cell roller until the viruses are sufficiently adsorbed to the cells. Then, a maintenance medium is added and incubation is continued at 30° C. until plenty of cytopathic effects may be observed. The roller bottle is then fastly shaken so that the virus-infected cells are peeled off the roller bottle and the cells are collected. The cells are separated from the cultured solution by low-speed centrifugation (1,000 to 3,000 rpm, 15 to 30 min.) or continuous centrifugation (12,000 rpm, 100 to 700 mL/min.). About 90% of the supernatant of cultured solution is removed by aspiration and the precipitates of cells are suspended in the remaining cultured solution by pipetting. The suspension is subject to sonication or freezing/thawing to disrupt cells. The cells are then separated from the cultured solution by centrifugation (1,000 to 3,000 rpm, 15 to 30 min.) to collect supernatant as a viral solution. This viral solution may be used for further culture as described above. The thus obtained viral solution may be used as a drug substance of vaccine. For the formulation of a vaccine, Polysorbate 80, peptone, amino acids and sugars e.g. sorbitol, lactose or sucrose are suitably selected and added as a stabilizing agent to the drug substance of vaccine. In case that sugars such as sorbitol, lactose or sucrose, which also act as fillers, are added, it may also be lyophilized as a product. For the live smallpox vaccine of the present invention, peptone and sorbitol are added to a drug substance of vaccine as stabilizing agents to prepare a final bulk. A colorless glass vial, preferably a 2 mL vial, washed and sterilized by dry heating, is filled with the final bulk, preferably with 0.5 mL of the final bulk in case of a 2 mL vial, and lyophilized to prepare a final product. The thus obtained vaccine according to the present invention contains 3% or less of revertants (MSP strain) and may be used as a safer vaccine.

Effects of MSP strain on the safety of vaccine may be studied by a skin growth test or by observing change in symptoms in small animals such as mice. In a skin growth test, rabbit is commonly used as being sensitive. The back buttocks of rabbit of 12 to 17 weeks old are unhaired and an amount of a drug substance of vaccine after suitable serial dilution is inoculated thereto intradermally. A diameter of rubefaction (eruption) formed in 2 to 5 days after inoculation is measured. As positive control, a parent strain of LC16m8 strain, i.e. LO strain or LC16m0 strain, may be used. Negative control may be a virus free medium or PBS. In the present invention, rubefaction of 10 mm or larger in a diameter is considered to be positive and a 50% dose of eruption ($ErD_{50}$) in each sample is calculated using Reed-Muench method (Masami Kurokawa et al., 1978, Bioassay, Kindai Shuppan Co., Ltd., p. 154 to p. 158) so that the safety may be evaluated by comparison of a 50% dose of eruption.

In case that effects of MSP strain on the safety of vaccine are evaluated with mice, mice of 3 to 5 days old may be used. More specifically, an amount of a drug substance of vaccine obtained by the present invention may be inoculated into the brain of mice. Positive control and negative control may be ones as described above. Survival of the animals within 21 days after inoculation is observed and a survival rate at Day 21 and a mean number of days of survival (days) are calculated for evaluation.

Alternatively, immunodeficient mice (hereinafter also referred to as "SCID mice") of 5 to 7 weeks old may also be used. More specifically, an amount of a drug substance of vaccine obtained by the present invention may be intraperitoneally inoculated to mice. A coat of hair, change in body weight, paralysis, pocks, abnormal behavior and survival are observed and scored for 25 to 30 days after inoculation so that effects of MSP strain on the safety may be evaluated with the total of scores. Positive control and negative control may be ones as described above.

The present invention is explained in more detail by means of the following Examples which are not intended to restrict a scope of the present invention in any sense.

Reference Example

Confirmation of Appearance of Revertant (MSP Strain) by Passaging (1) Trial of Isolation by Limiting Dilution Primary cells of rabbit kidney were prepared in T25 flasks until the cells formed a monolayer sheet and a highly diluted master viral seed solution was added thereto. The flasks were incubated at 30° C. until plenty of CPEs (cytopathic effects) were observed and then frozen at −80° C. After being frozen/thawed repeatedly three times, the viral solution obtained from each flask was measured for its content of MSP strain.

Those virus solutions, which contained MSP strain less than the limit of detection, were further inoculated into primary cells of rabbit kidney newly prepared in T25 flasks and incubated at 30° C. After 3 days of incubation, when plenty of CPEs were observed, the flasks were frozen at −80° C. After being frozen/thawed repeatedly three times, the viral solution obtained from each flask was further inoculated into primary cells of rabbit kidney newly prepared in T25 flasks and incubated at 30° C. The procedures aforementioned were repeated additionally three times and the viral solution obtained from each flask was measured for its content of MSP strain. The results are shown in Table 1. From the results, it was confirmed that a content of MSP strain, which exceeded the limit of detection appeared when passaging was repeated five times for a portion of LC16m8 strain virus obtained from a master viral seed solution by limiting dilution.

TABLE 1

| Sample | MSP titer ($Log_{10}PFU/mL$) |
| --- | --- |
| 8-1 | 4.48 |
| 8-4 | 4.95 |
| 8-7 | <4 (less than limit of detection) |
| 9-1 | 4.48 |

(2) Trial of Isolation by Plaque Cloning

Primary cells of rabbit kidney were prepared in a 6-well plate until the cells formed a monolayer sheet and a highly diluted master viral seed solution was added thereto and incubated at 30° C. Those clones with no MSP were collected and inoculated into primary cells of rabbit kidney prepared in T25 flasks and incubated at 30° C. After 3 days of incubation, when plenty of CPEs were observed, the flasks were frozen at −80° C. After being frozen/thawed repeatedly three times, the viral solution obtained from each flask was further inoculated to primary cells of rabbit kidney newly prepared in T25 flasks and incubated at 30° C. The procedures aforementioned were repeated additionally four times and the viral solution obtained from each flask was measured for its titer of MSP strain. The results are shown in Table 2. From the results, it was confirmed that a content of MSP strain, which exceeded the limit of detection, appeared when passaging was repeated five times for a portion of LC16m8 strain virus obtained from a master viral seed solution by plaque cloning.

TABLE 2

| Sample | MSP titer ($Log_{10}$PFU/mL) |
|---|---|
| 1-1 | 6.7 |
| 1-2 | 6.6 |
| 1-3 | 6.7 |
| 2-1 | <4.0 |
| 2-2 | 4.9 |
| 2-3 | <4.0 |
| 6-1 | <4.0 |
| 6-2 | 4.3 |
| 6-3 | 4.9 |
| 7-1 | <4.0 |
| 7-2 | 4.5 |
| 7-3 | 4.0 |
| 8-1 | <4.0 |
| 8-2 | 4.0 |
| 8-3 | 4.0 |
| 11-1 | 4.0 |
| 11-2 | <4.0 |
| 11-3 | <4.0 |
| 12-1 | <4.0 |

TABLE 2-continued

| Sample | MSP titer ($Log_{10}$PFU/mL) |
|---|---|
| 12-2 | <4.0 |
| 12-3 | 4.3 |
| 13-1 | <4.0 |
| 13-2 | <4.0 |
| 13-3 | <4.0 |

Example 1

Preparation of 1-Passaged Working Seed Solution

(1) Preparation with 6-Well Plate

The kidneys were sterilely removed from SPF rabbits of 7 days old and, after being washed with sterilized PBS/2ES, cut into pieces and put into a disperse solution. After being digested at 4° C. overnight while being stirred, the cells were again washed with PBS/2ES. The cells were collected by centrifugation and suspended in a growth medium resulting in a suspension of primary cells of rabbit kidney. The suspension was added to 24-well plates and incubated at 37° C. until the cells formed a monolayer sheet. A master viral seed solution was diluted with a maintenance medium and inoculated into each well at either of MOI=0.3, 0.1, 0.03, 0.01, 0.003, 0.001. Incubation was continued at 30° C. until plenty of cytopathic effects were observed. Subsequently, the cells were frozen in a freezer at −80° C. and, after being confirmed completely frozen, thawed under running water. The procedures from being frozen to being thawed were further repeated twice. A small amount of the viral solution was taken from each well and subject to detection test of MSP strain. Until the test results came out, the 24-well plate was again frozen in a freezer at −80° C. for storage.

For detection test of MSP strain, a monolayer sheet of Vero E6 cells was initially prepared in 6-well plates and either of viral solution which was diluted to $1\times10^2$, $3\times10^2$, or $1\times10^3$ was inoculated into the plates. After 1 hour of incubation at 35° C. at 5% $CO_2$ to let the virus be adsorbed to the cells, MEM containing 5% of inactivated FBS and 0.6% of agarose was overlaid. The plates were incubated in an incubator at 35° C. at 5% $CO_2$ for 2 days. After that, MEM containing 0.0025% of neutral red, 1% of inactivated FBS and 0.6% of agarose were further overlaid and the plates were incubated overnight in an incubator at 35° C. at 5% $CO_2$. Judgment was made based on the presence and number of plaques. Those individual samples where plaques did not appear at each of dilutions were selected as the individual samples containing a low content of MSP strain. The results are shown in Table 3. The selected individual samples were pooled after being thawed and defined as 1-passaged working seed solution.

A total viral titer of the obtained 1-passaged working seed solution was determined using RK-13 cells. A monolayer sheet of RK-13 cells was prepared in 6-well plates and a viral solution of the 1-passaged working seed solution diluted to either of $1\times10^4$, $1\times10^5$, or $1\times10^6$ was inoculated into the plates. After letting the virus be adsorbed to the cells for 1 hour in an incubator at 35° C. at 5% $CO_2$, MEM containing 5% of inactivated FBS and 0.6% of agarose was overlaid. The plates were incubated in an incubator at 35° C. at 5% $CO_2$ for 2 days. After that, MEM containing 0.0025% of neutral red, 1% of inactivated FBS and 0.6% of agarose was further overlaid and the plates were incubated overnight in an incubator at 35° C. at 5% $CO_2$. The numbers of plaques were counted and a titer value was calculated taking folds of dilution into consideration. A content ratio of MSP strain was determined as a ratio (%) of a titer of MSP strain to a total titer of viruses.

TABLE 3

| MOI at MVS inoculation | Well no. used for culture | Well no. selected | Content ratio (%) of MSP strain of 1-passaged working seed solution |
|---|---|---|---|
| 0.3 | 24 | 13 | 0.007 |
| 0.1 | 48 | 30 | 0.011 |
| 0.03 | 48 | 40 | 0.008 |
| 0.01 | 48 | 39 | 0.004 |
| 0.003 | 8 | 8 | 0.003 |
| 0.001 | 8 | 7 | 0.004 |

(2) Preparation with T25 Flask

A suspension of primary cells of rabbit kidney was prepared as described in Example 1(1). The suspension was added to T25 flasks and incubated at 37° C. until the cells formed a monolayer sheet. A master viral seed solution was diluted with a maintenance medium and inoculated into each flask at either of MOI=0.01, 0.003. Incubation was continued at 30° C. until plenty of cytopathic effects were observed. Subsequently, the cells were frozen in a freezer at −80° C. and, after being confirmed completely frozen, thawed under running water. The procedures from being frozen to being thawed were further repeated twice. A small amount of the viral solution was taken from each flask and subject to detection test of MSP strain. Until the test results came out, the T25 flasks were again frozen in a freezer at −80° C. for storage.

Detection test of MSP strain was done as described in Example 1(1). Those individual samples where plaques did not appear at each of dilutions were selected as the individual samples containing a low content of MSP strain. The selected individual samples were pooled after being thawed and defined as a 1-passaged working seed solution. A total viral titer of the obtained 1-passaged working seed solution and a content ratio of MSP strain were determined as described in Example 1(1). The results are shown in Table 4.

TABLE 4

| MOI at inoculation of master virus seed solution | Flask no. used for culture | Flask no. selected | Titer of 1-passaged working seed solution ($Log_{10}PFU/mL$) | Content ratio (%) of MSP strain of 1-passaged working seed solution |
|---|---|---|---|---|
| 0.01 | 50 | 7 | 7.8 | 0.009 |
| 0.003 | 50 | 18 | 7.8 | 0.007 |
|  |  | 25 | 7.8 | 0.009 |

Example 2

Preparation of 2-Passaged Working Seed Solution (1) Preparation with T150 Flask

A suspension of primary cells of rabbit kidney prepared as described in Example 1(1) was added to T150 flasks and incubated at 37° C. for 4 days. After being confirmed that the cells formed a monolayer sheet, the growth medium was removed by aspiration. After washing the cells with PBS/ES, the 1-passaged working seed solution obtained in Example 1(1) was diluted with a maintenance medium at either of MOI=0.1, 0.3, 1.0 and added to the flasks. Incubation was continued at 30° C. for 1 to 2 hours until the viruses were sufficiently adsorbed to the cells. Subsequently, a maintenance medium was added and incubation was continued at 30° C. until plenty of cytopathic effects were observed (3 days).

The containers were fastly shaken so that the virus-infected cells were peeled off the containers and the cells were collected. The cells were subject to centrifugation (1,200 rpm, 15 min.) and the supernatant was once removed. About ¹⁄₁₀ of the supernatant was filled back to the cell precipitates and the cell precipitates were suspended to the medium. Subsequently, the cell suspension was frozen in a freezer at −80° C. and, after being confirmed completely frozen, thawed under running water. The procedures from being frozen to being thawed were further repeated twice. After being thawed, the cell suspension was subjected to the centrifugation and the supernatant was pooled and defined as a 2-passaged working seed solution. Each total viral titer and each content ratio of MSP strain are shown in Table 5.

TABLE 5

| MOI at inoculation of 1-passaged working seed solution | Content ratio (%) of MSP strain of 1-passaged working seed solution | Titer of 2-passaged working seed solution ($Log_{10}PFU/mL$) | Content ratio (%) of MSP strain of 2-passaged working seed solution |
|---|---|---|---|
| 1.0 | 0.007 | 7.6 | 0.032 |
| 0.3 |  | 7.6 | 0.032 |
| 0.1 |  | 7.7 | 0.038 |
| 1.0 | 0.008 | 7.7 | 0.005 |
| 0.3 |  | 7.7 | 0.004 |
| 0.1 |  | 7.8 | 0.011 |
| 1.0 | 0.004 | 7.4 | 0.027 |
| 0.3 |  | 7.8 | 0.003 |
| 0.1 |  | 7.8 | 0.005 |

(2) Preparation with Roller Bottle

A suspension of primary cells of rabbit kidney prepared as described in Example 1(1) was added to roller bottles and incubated at 37° C. for 5 days. After being confirmed that the cells formed a monolayer sheet, the growth medium was removed by aspiration. After washing the cells with PBS/ES, the 1-passaged working seed solution obtained in Example 1(2) was diluted with a maintenance medium at either of MOI=0.1, 0.3, 1.0 and added to the bottles. Incubation was continued at 30° C. for 1 to 2 hours until the viruses were sufficiently adsorbed to the cells. Subsequently, a maintenance medium was added and incubation was continued at 30° C. until plenty of cytopathic effects were observed (3 days).

The containers were fastly shaken so that the virus-infected cells were peeled off the containers and the cells were collected. The cells were subject to centrifugation (3,000 rpm, 15 min.) and the supernatant was once removed. About ¹⁄₁₀ of the supernatant was filled back to the cell precipitates and the cell precipitates were suspended to the medium. Subsequently, the cell suspension was frozen in a freezer at −80° C. and, after being confirmed completely frozen, thawed under running water. The procedures from being frozen to being thawed were further repeated twice. After being thawed, the cell suspension was subjected to the centrifugation and the supernatant was pooled and defined as a 2-passaged working seed solution. Each total viral titer and each content ratio of MSP strain are shown in Table 6.

TABLE 6

| MOI at inoculation of 1-passaged working seed solution | Content ratio (%) of MSP strain of 1-passaged working seed solution | Titer of 2-passaged working seed solution ($Log_{10}$PFU/mL) | Content ratio (%) of MSP strain of 2-passaged working seed solution |
|---|---|---|---|
| 1.0 | 0.009 | 8.2 | 0.008 |
| 0.3 |  | 8.6 | 0.005 |
| 0.1 |  | 8.3 | 0.014 |
| 1.0 | 0.007 | 8.5 | 0.010 |
| 0.3 |  | 8.5 | 0.009 |
| 0.1 |  | 8.7 | 0.003 |
| 1.0 | 0.009 | 8.3 | 0.007 |
| 0.3 |  | 8.4 | 0.008 |
| 0.1 |  | 8.1 | 0.006 |

Example 3

Preparation of Drug Substance of Vaccine

A suspension of primary cells of rabbit kidney prepared as described in Example 1(1) was added to roller bottles and incubated at 37° C. for 5 days. After being confirmed that the cells formed a monolayer sheet, the growth medium was removed by aspiration. After washing the cells with PBS/ES, the 2-passaged working seed solution obtained in Example 2(1) or 2(2) was diluted with a maintenance medium at either of MOI=0.1, 0.3, 1.0 and added to the bottles. Incubation was continued at 30° C. for 1 to 2 hours until the viruses were sufficiently adsorbed to the cells. Subsequently, a maintenance medium was added and incubation was continued at 30° C. until plenty of cytopathic effects were observed (3 days).

The containers were fastly shaken so that the virus-infected cells were peeled off the containers and the cells were collected. The cells were subject to centrifugation (3,000 rpm, 15 min.) and the supernatant was once removed. About 1/10 of the supernatant was filled back to the cell precipitates and the cell precipitates were suspended to the medium. Subsequently, the cell suspension was frozen in a freezer at −80° C. and, after being confirmed completely frozen, thawed under running water. The procedures from being frozen to being thawed were further repeated twice. After being thawed, the cell suspension was subjected to the centrifugation and the supernatant was pooled and defined as a drug substance of vaccine. Each total viral titer and each content ratio of MSP strain as determined are shown in Table 7.

TABLE 7

| MOI at inoculation of 1-passaged working seed solution | Content ratio (%) of MSP strain of 1-passaged working seed solution | Titer of 2-passaged working seed solution ($Log_{10}$PFU/mL) | Content ratio (%) of MSP strain of 2-passaged working seed solution |
|---|---|---|---|
| 1.0 | 0.032 | 8.7 | 0.32 |
| 0.3 |  | 8.7 | 0.23 |
| 0.1 |  | 8.7 | 0.30 |
| 1.0 | 0.004 | 8.9 | 0.04 |
| 0.3 |  | 8.9 | 0.02 |
| 0.1 |  | 8.7 | 0.09 |
| 1.0 | 0.003 | 8.9 | 0.05 |
| 0.3 |  | 8.9 | 0.07 |
| 0.1 |  | 8.8 | 0.07 |
| 1.0 | 0.005 | 8.3 | 0.13 |

TABLE 7-continued

| MOI at inoculation of 1-passaged working seed solution | Content ratio (%) of MSP strain of 1-passaged working seed solution | Titer of 2-passaged working seed solution ($Log_{10}$PFU/mL) | Content ratio (%) of MSP strain of 2-passaged working seed solution |
|---|---|---|---|
| 0.3 |  | 8.2 | 0.18 |
| 0.1 |  | 7.9 | 0.36 |
| 1.0 | 0.009 | 8.3 | 0.07 |
| 0.3 |  | 8.3 | 0.12 |
| 0.1 |  | 8.2 | 0.11 |
| 1.0 | 0.008 | 8.4 | 0.07 |
| 0.3 |  | 8.3 | 0.06 |
| 0.1 |  | 8.2 | 0.10 |

Example 4

Effects of MSP Strain on Safety (1) Rabbit Skin Growth Test

The rabbits (Japanese white (JW), male) of 13 weeks old weighing 2.5 to 3.1 kg were unhaired through back to buttons and each 0.1 mL of test samples (MSP content: 0.001%, 0.3%, 2.1%, 3.2%, 10.8%) subjected to 10-fold serial dilution with a suspension medium were inoculated thereto intradermally at $1\times10^2$, $1\times10^3$, $1\times10^4$, or $1\times10^5$ PFU/mL. Inoculation was made to 3 rabbits for each dilution of the viral solutions at two sites/rabbit. The diameter of rubefaction (eruption) formed 3 days after inoculation was measured and the diameter of 10 mm or more was considered to be positive. The 50% dose of eruption ($ErD_{50}$) in each sample was calculated using Reed-Muench method. The results are shown in Table 8. Values of $ErD_{50}$ ($ErD_{50}=10^n$) were analyzed using Savege test (rank test). As a result, no significant difference was observed among viral solutions containing 0.001 to 3.2% MSP strain.

TABLE 8

| Virus | LC16m8 | | | | | LC16mO | LO |
|---|---|---|---|---|---|---|---|
| MSP content (%) | 0.001% | 0.3% | 2.1% | 3.2% | 10.8% | | |
| $ErD_{50}$ | 4.5 | 4.5 | 4.5 | 4.2 | 3.5 | <1.0 | 1.0 |

(2) Inoculation to SCID Mice

Figure 2:
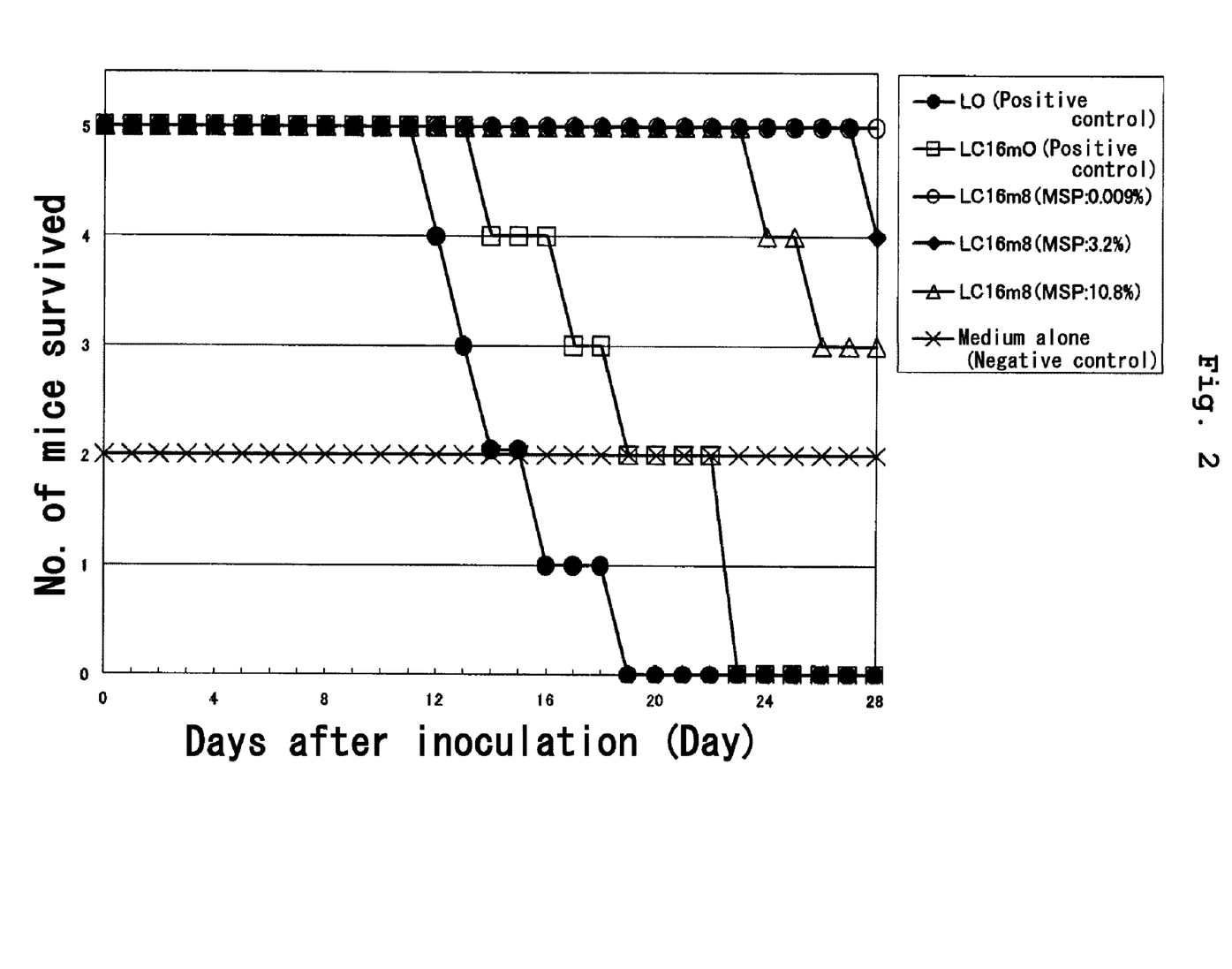
FIG. 2 is a graph showing a survival curve of SCID mice after inoculation of the virus in the SCID mouse intraperitoneal inoculation study.
Figure 3:
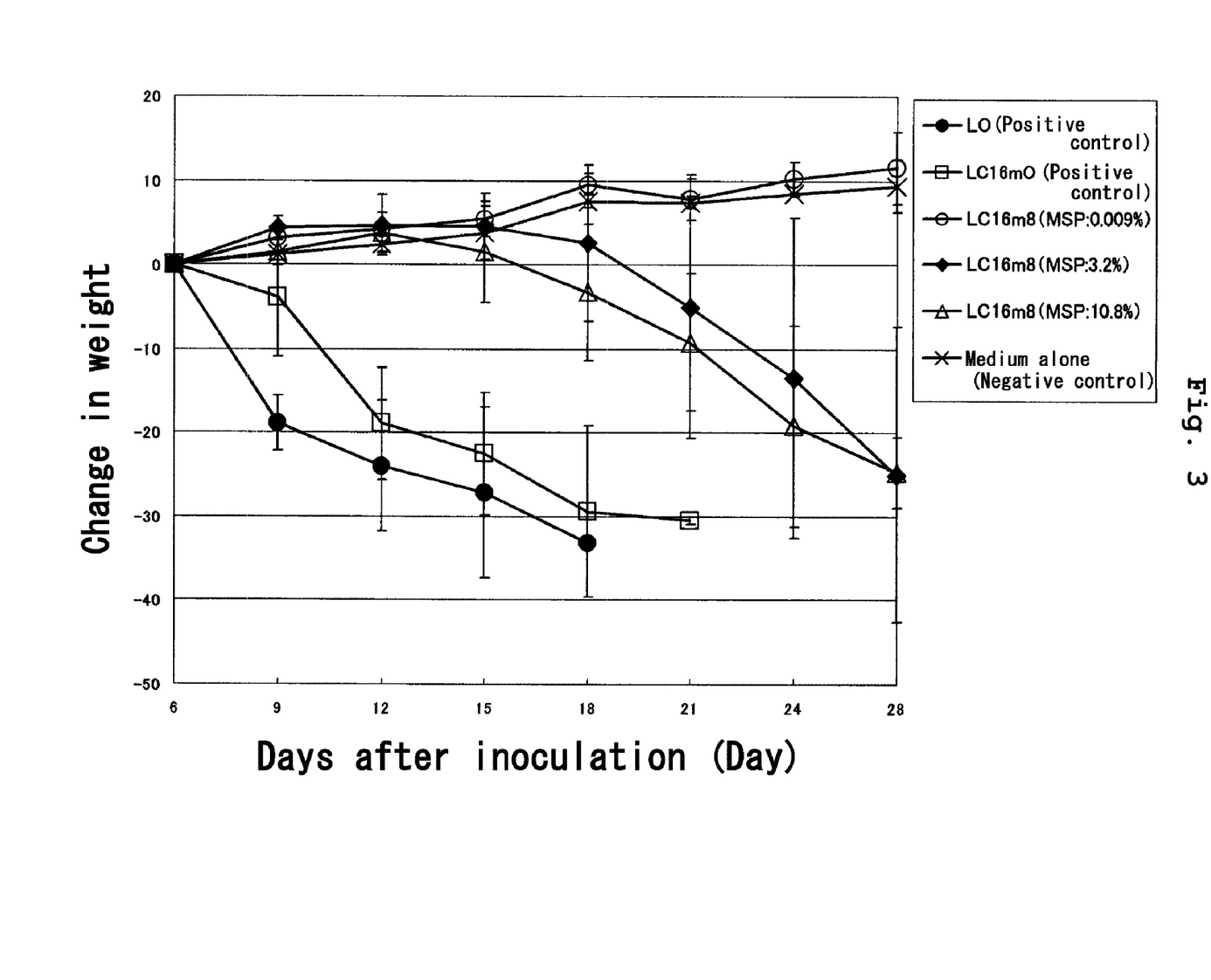
FIG. 3 is a graph showing the changes in body weight of SCID mice after inoculation of the virus in the SCID mouse intraperitoneal inoculation study.

Each 0.5 mL of test samples (MSP content: 0.009%, 3.2%, 10.8%) diluted with a suspension medium to $10^{7.3}$ PFU/mL or $10^{5.6}$ PFU/mL were inoculated intraperitoneally to SCID mice of 6 weeks old (male; C.B-17/Icr Crj-scid/scid; 5 mice/group). The mice were observed for 28 days after inoculation and the survival rate and the mean duration (days) of survival were calculated. While observation, symptoms of each individual subject were evaluated with scoring criteria shown in Table 9 and the total score per inoculated samples at each day was calculated. Furthermore, the mice were weighed every 3 days (in part, every 4 days) from Day 8 after initiating observation. The average of body weight per inoculated samples at each day was calculated and then the rate of change in body weight compared to the average of body weight at the date of initiating observation (Day 6) was calculated. The results are shown in FIGS. 2 and 3.

TABLE 9

| Score | Symptoms |
|---|---|
| 0 | No symptom |
| 1 | Out of order in coat of hair, eruption, uneasy behavior |
| 2 | Inversed hair, pocks (no suppuration) |
| 3 | Pocks (with suppuration), falling-off of hair, crouching, loss of strength |
| 4 | Paralysis, jumping, abnormal behavior (staggering etc.) |
| 5 | Death |

INDUSTRIAL APPLICABILITY

According to the present invention, a safer live smallpox vaccine, which contains lowered content of revertants, may be prepared.

The invention claimed is:

1. A process for preparing a working seed solution of a vaccine containing as an active ingredient a mutant virus that is likely to generate revertants, which comprises the following steps (1) to (3):
   (1) inoculating a solution of a mutant virus to 1 to n containers, wherein n is an integer, of an isolated animal cell and incubating them;
   (2) diluting a portion of the cultured solution from each container and inoculating the diluted solution to RK-13 cells and to Vero cells and incubating them; and
   (3) selecting containers which contain a cultured solution that forms plaques in RK-13 cells but does not form plaques in Vero cells and pooling each cultured solution obtained from selected containers.

2. The process of claim 1, wherein a viral content of the diluted solution in (2) above is $1\times10^4$ PFU or more.

3. The process of claim 1, wherein the isolated animal cell is a primary cell.

4. The process of claim 3, wherein the primary cell is derived from rabbit kidney.

5. The process of claim 1, wherein the mutant virus is an attenuated vaccinia virus.

6. The process of claim 5, wherein the attenuated vaccinia virus is the LC16m8 strain.

7. A process for manufacturing a smallpox vaccine, which comprises inoculating the working seed solution obtained through the process of claim 5 above to an isolated animal cell, incubating and then collecting a viral solution from the culture.

8. The process of claim 7, wherein the concentration is a MOI of 0.001 to 5, at which the working virus solution is inoculated, and wherein the number of the isolated animal cells is $1\times10^5$ to $1\times10^{12}$.

9. The process of claim 7, wherein the animal cell is a primary cell.

10. The process of claim 9, wherein the primary cell is derived from rabbit kidney.

11. The process of claim 8, wherein the MOI is 0.1 to 1.

12. The process of claim 8, wherein the number of the isolated animal cells is $0.5\times10^8$ to $3\times10^8$.

* * * * *